United States Patent
Hall

(10) Patent No.: US 9,873,902 B2
(45) Date of Patent: Jan. 23, 2018

(54) METHODS AND APPARATUS FOR DETERMINING ANALYTE IN A SAMPLE USING A SENSOR HAVING ELECTRODES WHICH ARE PROVIDED WITH AN ENZYME AND A MEDIATOR

(71) Applicant: SureSensors Ltd., Inverness (GB)

(72) Inventor: Geoffrey Frank Hall, Ross-shire (GB)

(73) Assignee: SURESENSORS LIMITED, Inverness (GB)

( * ) Notice: Subject to any disclaimer, the term of this patent is extended or adjusted under 35 U.S.C. 154(b) by 46 days.

(21) Appl. No.: 14/898,638

(22) PCT Filed: Jun. 17, 2014

(86) PCT No.: PCT/EP2014/062747
§ 371 (c)(1),
(2) Date: Dec. 15, 2015

(87) PCT Pub. No.: WO2014/202625
PCT Pub. Date: Dec. 24, 2014

(65) Prior Publication Data
US 2016/0186229 A1    Jun. 30, 2016

(30) Foreign Application Priority Data

Jun. 18, 2013 (GB) .................................. 1310819.6

(51) Int. Cl.
*G01N 27/327* (2006.01)
*C12Q 1/00* (2006.01)
(52) U.S. Cl.
CPC ......... *C12Q 1/006* (2013.01); *G01N 27/3271* (2013.01); *G01N 27/3273* (2013.01); *G01N 27/3274* (2013.01); *G01N 27/3277* (2013.01)

(58) Field of Classification Search
CPC ....................... G01N 27/3273; G01N 27/3274
See application file for complete search history.

(56) References Cited

U.S. PATENT DOCUMENTS

| 4,260,680 A | 4/1981 | Muramatsu et al. |
| 6,413,398 B1 | 7/2002 | Gerhardt et al. |
| (Continued) | | |

FOREIGN PATENT DOCUMENTS

| EP | 0396788 | 11/1990 |
| EP | 1840219 | 10/2007 |
| (Continued) | | |

*Primary Examiner* — Alexander Noguerola
(74) *Attorney, Agent, or Firm* — Knobbe Martens Olson & Bear, LLP

(57) ABSTRACT

The invention relates to a method of and apparatus for determining concentration of an analyte, such as glucose, in a fluid sample, such as body fluid or control solution, using a mediated redox reaction. In particular, the method relates to mitigation of the effects of haematocrit on the response of sensor device used in such a method or apparatus. The invention describes a method of determining concentration of an analyte in a fluid sample deposited on a sensor device having a working electrode and a counter electrode, in which the electrodes are provided with an enzyme and a mediator for carrying out a mediated redox reaction, the method comprising: applying a first oxidizing potential between the working and counter electrodes during a first time period; applying a second reducing potential between the working and counter electrodes during a second time period; determining a reaction parameter, the reaction parameter being indicative of the concentration of reduced mediator at the counter electrode after commencement of the second time period; using the reaction parameter to determine the concentration of analyte.

20 Claims, 12 Drawing Sheets

(56) References Cited

U.S. PATENT DOCUMENTS

| | | |
|---|---|---|
| 6,576,117 B1 | 6/2003 | Iketaki et al. |
| 7,288,174 B2 | 10/2007 | Cui et al. |
| 8,617,370 B2 * | 12/2013 | Chatelier ............... C12Q 1/005 204/403.01 |
| 2004/0260511 A1 | 12/2004 | Burke et al. |
| 2007/0074977 A1 | 4/2007 | Guo et al. |
| 2007/0240998 A1 | 10/2007 | Cheng et al. |
| 2008/0000780 A1 | 1/2008 | Tonks |
| 2008/0179197 A1 | 4/2008 | Wu |
| 2008/0099347 A1 | 5/2008 | Barlag et al. |
| 2010/0258451 A1 | 10/2010 | Adlassnig |
| 2012/0205259 A1 | 8/2012 | Iyengar et al. |
| 2013/0001103 A1 | 1/2013 | Chatelier et al. |
| 2013/0098776 A1 | 4/2013 | Hsu |
| 2013/0118920 A1 | 5/2013 | Craggs et al. |
| 2014/0027312 A1 | 1/2014 | Macfie et al. |

FOREIGN PATENT DOCUMENTS

| | | |
|---|---|---|
| EP | 2042865 | 4/2009 |
| EP | 2098857 | 9/2009 |
| EP | 2138841 | 12/2009 |
| GB | 2296333 | 6/1996 |
| WO | WO 01/57510 | 8/2001 |
| WO | WO 03/097860 | 11/2003 |
| WO | WO 2007/013915 | 2/2007 |
| WO | WO 2007/121111 | 10/2007 |
| WO | WO 2008/040998 | 10/2008 |
| WO | WO 2012/035297 | 3/2012 |
| WO | WO 2012/084194 | 6/2012 |
| WO | WO 2013/030375 | 3/2013 |
| WO | WO 2013/164632 | 11/2013 |
| WO | WO 2014/016578 | 1/2014 |

\* cited by examiner

Illustrates some alternative strip designs but the electrode dimensions may vary Figres 1a and 1b illustrates some alternative strip designs but the electrode dimensions may vary Chart showing applied potential and timing of example assay A glucose calibration was carried out at 8 glucose levels in 47% haematocrit venous blood with triplicate measurements at each level. Mean responses are shown in Figure 4

Transients from 3 reps, 566mg/dL glucose 47% hct

Cumulative charge passed between 6.5 and 7.0 seconds at 5 hct levels at 527 mg/dL Dependence of calibration slope on sample hct using current at 4 seconds as the response Average strip responses at 5 hct levels and 527 mg/dL glucose, n=4.

The assay method can also use different timings for the phases of the assay. For example Figure 10 illustrates the calibration curve obtained using a 3 second phase 1 followed by a 2 second phase 2:

Calibration curve for assay with 3 sec phase 1 and 2 sec phase 2

Effect of haematocrit on response from 520 mg/dL glucose blood

Illustrative plot of anticipated ferrocyanide concentration gradients at the counter electrode at the end of Phase 1

Phase 1 reactions

Phase 2 reactions

Method flow with both measurement and background electrodes as shown in Figure 1b.

METHODS AND APPARATUS FOR DETERMINING ANALYTE IN A SAMPLE USING A SENSOR HAVING ELECTRODES WHICH ARE PROVIDED WITH AN ENZYME AND A MEDIATOR

FIELD OF THE INVENTION

The invention relates to a method of and apparatus (and metering device, sensor device and kit) for determining concentration of an analyte, such as glucose, in a fluid sample, such as body fluid or control solution, using a mediated redox reaction. In particular, the method relates to mitigation of the effects of haematocrit on the response of a sensor device used in such a method or apparatus.

This application claims priority from UK patent application No. GB1310819.6 filed on 18 Jun. 2013, the entire contents of which are here by incorporated by reference. In particular, if any subject matter or features are present in the priority application UK patent application No. GB1310819.6 and are not, for whatever reason, present in this application, such subject matter and features are specifically incorporated by reference into this application and may be claimed. Such features, if any, can be precisely defined and are identifiable by comparison between this application and the priority application and are thought to contribute to solving the technical problem underlying the invention.

BACKGROUND

There are two basic approaches available to designing glucose sensor devices that do not suffer from the effects of haematocrit interference. Either the haematocrit of the sample can be measured independently of the glucose measurement, and the glucose measurement is then corrected by a predetermined factor for the measured haematocrit, or the sensor and/or its operation are designed in a way that the glucose measurement is not substantially affected by the haematocrit of the sample in the first place so as to provide a more haematocrit independent measurement. To measure haematocrit and glucose separately, and then correct the glucose measurement using the haematocrit measurement, relies on accurate haematocrit measurement being possible, or else more error may be introduced into the result than is removed.

The simpler method is to devise an haematocrit independent measurement system.

WO2008040998 CARDOSI et al describes applying a plurality of voltages over respective durations to correct for heamatocrit. The analysis used appears somewhat complex. Application of a reverse potential for fill detection is described.

U.S. Pat. No. 6,576,117 IKETAKI describes application of a predetermined voltage twice to promote an electrochemical reaction and correct for errors. The analysis used appears somewhat complex.

WO2012035297 CRAGGS et al describes haematocrit compensation by estimating haematocrit corrected analyte concentration from first, second, third, fourth and fifth test currents. The analysis used appears somewhat complex.

WO2007013915 WU et al describes gated amperometric pulse sequences to provide shorter analysis time and/or improved accuracy and/or precision of analysis.

U.S. Pat. No. 7,288,174 CUI describe using water soluble fatty acid to reduce the haematocrit level dependent bias and US2005/000808 CUI describes an electrochemical biosensor.

Further art includes US2014/0027312 and WO2014/016578 both to MACFIE, (published after the priority date of this application), WO2013/164632 MCNEILAGE, (published after the priority date of this application), US2010/0258451 ADLASSING, WO2012/084194 BURKE, EP2138841 HODGES, US2008/000780 TONKS, GB2296333 MATTHIESSEN, US2004/0260511 BURKE, EP0396788 KUYPERS, U.S. Pat. No. 6,413,398 GERHARDT and US2013/098776 HSU, EP2098857 CHATALIER, EP2042865 CHATALIER, WO2007/121111 POPOVICH, EP1840219 CHATALIER, WO01/57519 O'HARA.

The above art describes examples of both approaches. None are very satisfactory, being too complex and/or requiring adaptation of manufacturing processes. There is therefore a need to provide a simpler approach to mitigation of the effects of haematocrit. Furthermore there is an ongoing need to provide improved haematocrit independent measurement systems and mitigation methods that more accurately reduce the effect of or account for haematocrit level dependent effects in sensor device responses.

The present invention seeks to alleviate one or more of the above problems. Further, the invention aims to provide, in one or more embodiments, a method (and apparatus, metering device, sensor device and kit) for measurement of analyte concentration that is more independent of haematocrit concentration than the prior art and, in particular embodiments, is preferably largely independent of haematocrit concentration, or, more preferably, substantially independent of haematocrit concentration.

STATEMENTS OF THE INVENTION

In a first aspect of the invention, there is provided a method of determining concentration of an analyte in a fluid sample deposited on a sensor device having a working electrode and a counter electrode, in which the electrodes are provided with an enzyme and a mediator for carrying out a mediated redox reaction, the method comprising:
    applying a first oxidising potential between the working and counter electrodes during a first time period;
    applying a second reducing potential between the working and counter electrodes during a second time period;
    determining a reaction parameter, the reaction parameter being indicative of the concentration of reduced mediator at the counter electrode after commencement of the second time period;
    using the reaction parameter to determine the concentration of analyte.

Thus, the reaction parameter is a parameter indicative of the concentration of reduced mediator found at the counter electrode after commencement of the second time period. It may be determined in various ways e.g. measured directly, or it may be determined from a measurement parameter comprising one or more measurements taken during, or before and during, the second time period.

In a second aspect of the invention there is provided an apparatus for determining concentration of analyte in a fluid sample comprising:
    a sensor device having a working electrode and a counter electrode, in which the electrodes are provided with an enzyme and a mediator;

a detector to determine a reaction parameter indicative of the concentration of reduced mediator at the counter electrode after commencement of the second time period; and a microprocessor to control application of a first oxidising potential between the working electrode and the counter electrode for a first time period, and a second reducing potential between the working electrode and the counter electrode for a second time period.

Preferably, the second aspect comprises a meter device comprising the detector and the microprocessor.

In a third aspect there is provided a metering device for carrying out a method according to the invention comprising the apparatus according to the invention. Preferably, in a third aspect of the invention there is provided a meter device for carrying out a method according to the invention which comprises: a detector to determine a reaction parameter indicative of the concentration of reduced mediator at the counter electrode after commencement of the second time period; and a microprocessor to control application of a first oxidising potential between the working electrode and the counter electrode for a first time period, and a second reducing potential between the working electrode and the counter electrode for a second time period.

In a fourth aspect there is provided a kit comprising a metering device according to the invention and a test sensor for use with the meter, and/or instructions for carrying out the method(s) of the invention.

Several embodiments of the invention are described and any one or more features of any one or more embodiments may be used in any one or more aspects of the invention as described above. Various alternative embodiments will be apparent to those skilled in the art from the disclosure of the present application, all such embodiments are intended to fall within the scope of the present application. For example, various times for the first and second time periods are described and it will be apparent to those skilled in the art that variations on these time periods are possible, for example, within the overall aim of a short overall test time.

Preferably, a reaction parameter is determined from one or more measurements made only after commencement of the second phase is used to determine the concentration of analyte. Preferably, a reaction parameter is determined from one or more measurements made only after commencement of the second time period.

Preferably a reaction parameter is determined in respect of (e.g. during) a third time period, which preferably commences after the start of the second time period.

Preferably, a reaction parameter is determined from one or more measurements made during a third time period.

Preferably, the third time period ends at substantially the same time as the end of the second time period during which the second reducing potential is applied.

Preferably, the method comprises determining a reaction parameter comprises measuring a measurement parameter comprising one or more measurements.

Preferably, the measurement parameter is measured at at least one time point.

Preferably, the measurement parameter is measured at at least three time points.

Preferably, the measurement parameter is measured quasi-continuously over substantially all the third time period.

Preferably, the measurement parameter is measured continuously over substantially all the third time period.

Preferably, the measurement parameter is a current.

Preferably, the reaction parameter is a charge passed via the working and/or counter electrode during a predetermined time period.

Preferably the reaction parameter is a charge, optionally a cumulative charge, passed via the working and/or counter electrode during or in respect of a third time period.

Preferably, the predetermined time period is the third time period.

Preferably, the charge passed is determined over a predetermined time period comprising the third time period.

Preferably, the predetermined time period is a sub-period comprising a portion of the third time period.

Preferably, the charge passed is determined over a predetermined time period comprising at least one sub-period comprising a portion of the third time period.

Preferably, charge passed is determined by measuring the current during the third time period or during one or more sub-periods comprising a portion of the third time period.

Preferably, the reaction parameter is determined
  by calculating the difference between the total charge passed up to the start of the third time period and the total charge passed up to the end of the third time period and/or
  by calculating the total charge passed during the third time period from charge passed during two or more sub-periods each comprising a portion of the third time period and as a whole comprising substantially all the third time period.

Preferably, the reaction parameter is determined by calculating the magnitude of the difference.

Preferably, with respect to the counter electrode, the first oxidising potential is positive on the working electrode, and the second reducing potential is negative on the working electrode.

Preferably, the magnitude of the first oxidising potential is greater than or equal to the magnitude of the second reducing potential.

Preferably, at least two working electrodes and/or at least two counter electrodes are used to determine the reaction parameter.

Preferably, the duration of the first time period is of the same order as the duration of the second time period.

Preferably, the duration of the first time period is greater than or equal to the length of the second time period.

Preferably, the duration of the first time period is greater than or equal to the duration of the second time period, and/or the duration of a second time period is greater than the duration of a third time period, and, optionally, the third time period ends at the same time as the second time period.

Preferably, the duration of the first and second time periods are of the order of a few seconds.

Preferably, the duration of the first time period is about 2 to about 9 seconds, or about 3 to about 6 seconds, or about 3 to about 5 seconds or is 1 to 5 seconds or is 2 to 9 seconds or is 3 to 6 seconds or is 3 to 5 seconds.

Preferably, the duration of the second time period is about 1 to about 9 seconds, or about 2 to about 5 seconds, or about 2 to about 4 seconds or is 0.1 to 4 seconds or is 1 to 9 seconds or is 2 to 5 seconds or is 2 to 4 seconds.

Preferably, the duration of the first time period is about 5 seconds and the duration of the second time period is about 4 seconds, or the duration of the first time period is about 3 seconds and the duration of the second time period is about 2 seconds, or the duration of the first time period is about 3 seconds, or is 3 seconds, and the duration of the second time period is about 1 second, or is 1 second.

Preferably, the duration of the third time period is between about 0.05 seconds and about 2 seconds, is between about 0.1 seconds and about 1 second, is between about 0.2 seconds and 0.8 seconds, is about 0.5 seconds, is the final 0.5 second of the second time period, is 0.05 seconds and 2 seconds, is between 0.1 seconds and 1 second, is between 0.2 seconds and 0.8 seconds, is 0.5 seconds.

Preferably, the duration of the first time period is about 1 to about 3 seconds longer, or about 1 to about 2 seconds longer, or is 1 to 3 seconds longer or is 1 to 2 seconds longer, than the duration of the second time period.

Preferably, the third time period commences after a delay of about 0.1 to 5 seconds, about 1 to 3 seconds, about 1 to about 2 seconds, 0.1 to 5 seconds, 1 to 3 seconds, 1 to 2 seconds, following the start of the second time period.

Preferably, the working electrode has substantially the same surface area as the counter electrode.

Preferably, the counter electrode is at least 1.5 fold, is at least 2 fold, is at least 4 fold, is at least 6 fold, is at least 8 fold, is at least 10 fold the area of the working electrode.

Preferably, the first time period is at least about 1 second, at least about 2 seconds, at least about 3 seconds, at least about 4 seconds, at least about 5 seconds, at least about 6 seconds, at least about 7 seconds, at least about 8 seconds, at least about 9 seconds, at least about 10 seconds, at least 1 second, at least 2 seconds, at least 3 seconds, at least 4 seconds, at least 5 seconds, at least 6 seconds, at least 7 seconds, at least 8 seconds, at least 9 seconds, at least 10 seconds.

Preferably, the second time period is at least about 1 second, at least about 2 seconds, at least about 3 seconds, at least about 4 seconds, at least about 5 seconds, at least about 6 seconds, at least about 7 seconds, at least about 8 seconds, at least about 9 seconds, at least about 10 seconds, at least 1 second, at least 2 seconds, at least 3 seconds, at least 4 seconds, at least 5 seconds, at least 6 seconds, at least 7 seconds, at least 8 seconds, at least 9 seconds, at least 10 seconds.

Preferably, the redox reaction enzyme is selected from the list comprising lactate dehydrogenase, alcohol dehydrogenase, hydroxybutyrate dehydrogenase, cholesterol oxidase, amino acid oxidase, pyruvate oxidase, peroxidase, sarcosine oxidase, lactate oxidase, alcohol oxidase, monoamine oxidase, glycerol oxidase, glycerol phosphate oxidase, urate oxidase, xanthine oxidase, ascorbate oxidase, catalase, diaphorase, glucose dehydrogenase, glucose oxidase.

Preferably, the mediator is selected from the list comprising potassium ferricyanide, ferrocene derivatives, phenoxazine derivatives, phenothiazine derivatives, quinone derivatives, and reversible redox transition metal complexes, particularly those of Ruthenium and Osmium, nicotinamide adenine dinucleotide (phosphate), diimines, phenanthroline derivatives, dichlorophenolindophenol, tetrazolium dyes.

Preferably, the target substance or analyte is selected from the list comprising glucose, cholesterol, ethanol, creatinine, creatine, ascorbic acid, uric acid, hydrogen peroxide.

Preferably, the fluid sample is selected from the list comprising blood, plasma, serum, saliva, urine, cerebrospinal fluid, semen, tear fluid, ascites.

Preferably the method comprises:
  providing a second working electrode and second counter electrode provided with mediator but not enzyme;
  carrying out the steps of any of claims 1 to 36, 38 or 39 on the second working electrode and second counter electrode;
  determining a background parameter indicative of the concentration of reduced mediator at the second counter electrode after commencement of the second time period; and
  using the background parameter to correct one or more of a measurement parameter, a reaction parameter, concentration of analyte.

Preferably, a water soluble dry reagent film comprising enzyme and mediator is provided overlaying the working and counter electrodes, the dry reagent film having two exposed generally parallel opposing surfaces before being laid down.

Preferably, the apparatus comprises the same or a different microprocessor for determining the concentration of analyte using the reaction parameter.

Optionally, the invention comprises various aspects and embodiments of the invention, such as the method, apparatus, meter device, sensor device and kit, in which any feature which cannot, explicitly or implicitly, be directly and unambiguously derived using common general knowledge from the priority application GB1310819.6 as filed, is expressly excluded from that aspect or embodiment of the invention as claimed.

BRIEF DESCRIPTION OF THE FIGURES

The invention will now be described, by way of example only, with reference to the following figures in which like reference numerals refer to like features.

DETAILED DESCRIPTION OF THE INVENTION

Figure 1A:
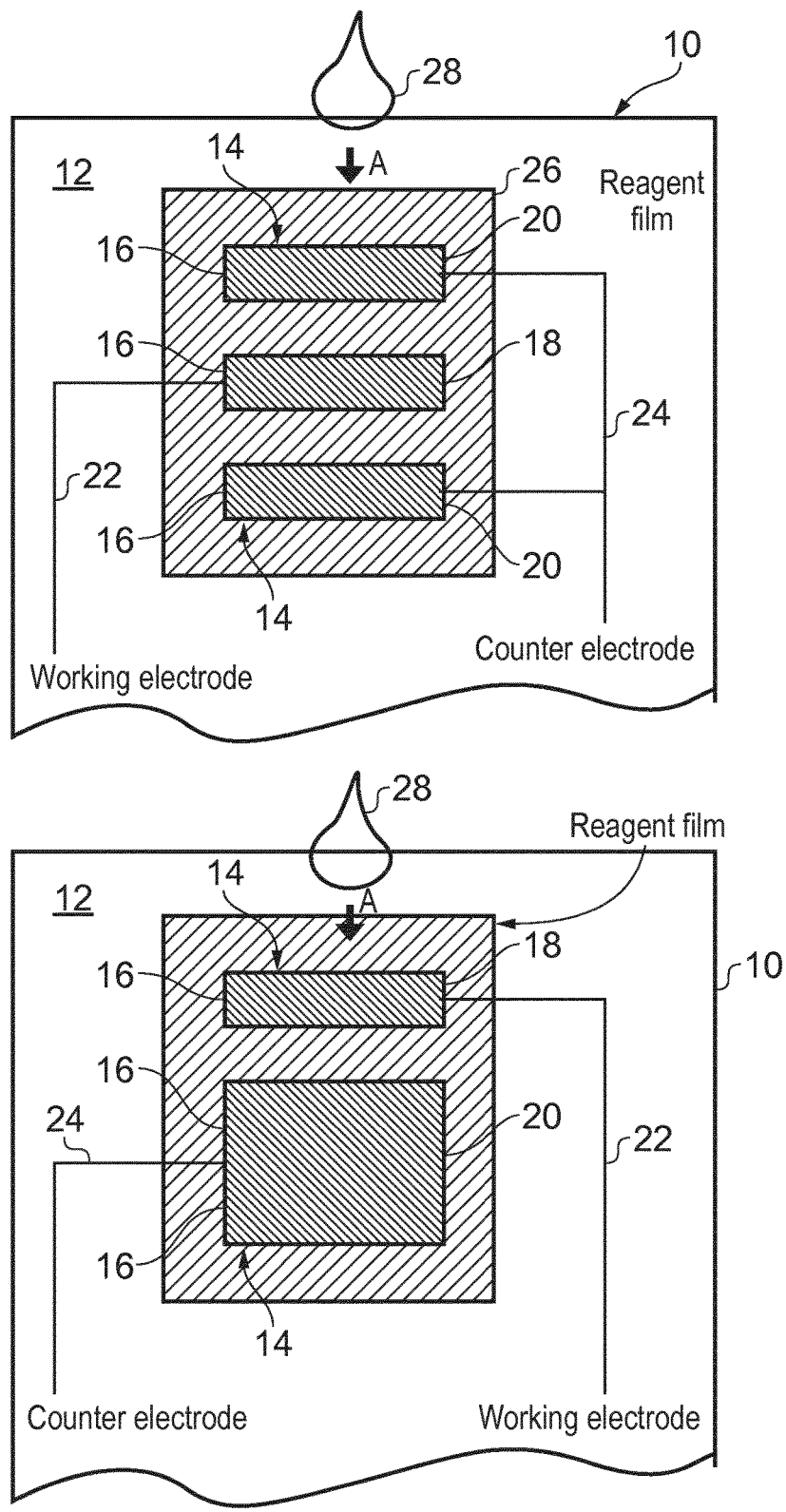
FIG. 1A shows schematic plan views of two sensor devices (e.g. test strips) with different arrangements of working and counter electrode(s) both provided with enzyme and mediator.

FIG. 1A illustrates one of two example sensor devices 10 (e.g. for determination of analyte concentration such as glucose test strips) which can be used in the methods and apparatus of the invention, each having a substrate 12 on which a conductive layer 14 is overlaid, conductive layer 14 comprising a number of separate measurement electrodes 16. The first sensor device 10 has a single working electrode 18 and a two-part counter electrode 20 (formed from two measurement electrodes 16 electrically connected together). Each of the measurement electrodes 16 forming working electrode 18 and the parts of counter electrode 20 are of similar area, the area of the counter electrode preferably being consequently twice that of the working electrode. Preferably the counter electrode is larger than the working electrode for reasons as understood by those skilled in the art. The second sensor device 10 has a single working electrode 18 and a single counter electrode 20 of larger area than working electrode 20. Typically, counter electrode 20 has about twice the area of working electrode 18 in total, although other ratios of areas may be possible as described elsewhere herein. An insulation layer (not illustrated) typically defines a channel, typically a capillary channel through which a fluid sample 28 can flow over the measurement electrodes 16.

The fluid channel (not shown) may have an opening at the end edge or side edge of the device 10 or on the top of device 10. The device 10 may be in the form of a test strip (being relatively thin and planar) and may be elongate, e.g. rectangular, but other strip shapes may be used. Conductive traces 22, 24 connect working electrode 18 and counter electrode 20, respectively, to a computing device preferably in the form of a portable metering device (not shown). The metering device typically contains a microprocessor and associated electronics for applying potentials to the measurement electrodes in accordance with the method(s) of the invention and also preferably for measuring one or more measurement parameter(s) and/or measuring and/or determining one or more reaction parameters indicative of the concentration of reduced mediator at the counter electrode after the commencement of a second time period as will be described below for determining the concentration of an analyte in a fluid sample. Preferably the microprocessor of the metering device also determines the analyte concentration from the reaction parameter.

Reagent 26 is typically provided as a layer overlaying the working electrode(s) 18 and the counter electrode(s) 20. It is of note that whilst only one working electrode or counter electrode may be shown, the invention may be applied to sensor devices having two or more working electrodes or counter electrodes (e.g. to repeat the method and take an average and/or as background electrodes to provide for background correction as will be described later). Reagent 26 may be deposited wet by wet deposition techniques spreading out to form a layer which is dried, or may be deposited dry, for example, by depositing a water soluble dry reagent film having two exposed, generally parallel opposing surfaces before it is laid down on substrate 12 to become a layer. Such a water soluble dry reagent layer is described in the present applicant's co-pending application WO2011012848, the contents of which are incorporated herein by reference.

Thus, one or more additional measurement electrodes e.g. additional working electrodes and/or counter and/or reference electrodes may be provided without departing from the scope of the invention. For example, a second working electrode may be provided as a fill detect electrode (typically placed after the first working electrode in the direction of flow). A background working electrode, and optionally also a background counter electrode, both absent active reagent 26 may also be provided and the response (e.g. either current at the end of the first time period or more preferably charge passed during third time period via the background working electrode and/or counter electrode) may be subtracted or otherwise used to correct any parameter measured or determined according to the methods of the present invention.

Figure 1B:
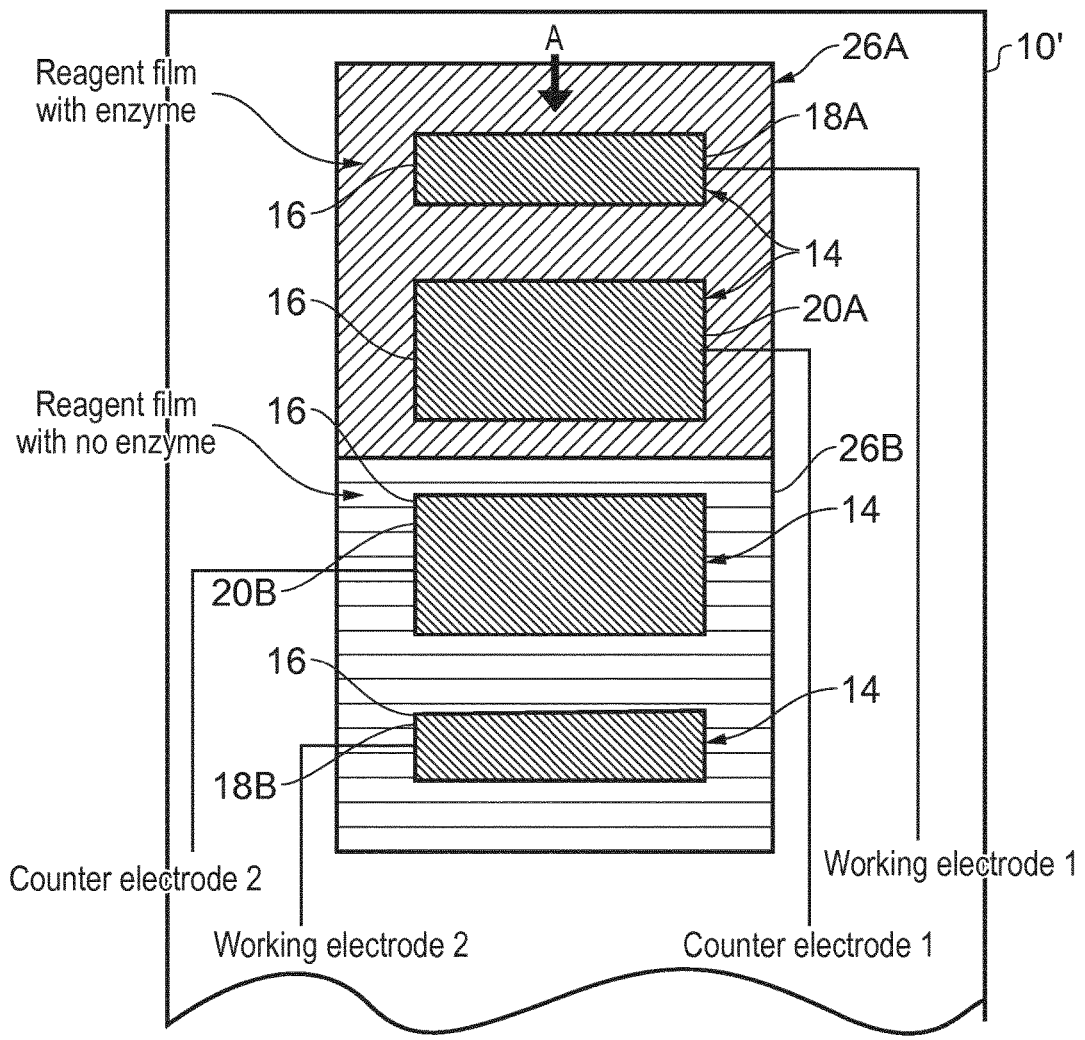
FIG. 1B shows a schematic plan view of an alternative sensor device with a first working electrode and a first counter electrode both provided with enzyme and mediator, and having a second working electrode and second counter electrode provided with mediator but no enzyme.

FIG. 1B shows an alternative sensor device to that seen in FIG. 1A having four measurement electrodes 16 comprising in the direction of fluid flow A, a first working electrode 18A, a first counter electrode 20A both overlaid by a first reagent layer, here a film 26A, comprising enzyme and mediator and a second counter electrode 20B and a second working electrode 18B both overlaid by a second reagent layer, here a film 26B, having no enzyme or no active enzyme and comprising a mediator.

Thus, FIG. 1B shows an example embodiment of an alternative sensor device 10 having first working and first counter electrodes 18A, 20A provided with active reagent containing enzyme and second working and second counter electrodes 18B, 20B provided with mediator but inactive reagent containing no enzyme or inactive enzyme. Thus, second working and second counter electrodes 18B, 20B function as background electrodes.

In use, a fluid sample, e.g. a drop of blood 28, is deposited on sensor device 10 and travels and/or spreads over the measurement electrodes 16, in the direction of arrow A for example, typically via capillary action.

In the following description of the methods of the invention, reference will be made to measurement of glucose concentration in blood and measurement of the blood glucose concentration via a mediated redox reaction using glucose dehydrogenase (GDH) as enzyme and ferricyanide as mediator. It is to be understood that other mediated redox reaction schemes may be used to measure the same or different analytes as would be understood by those skilled in the art. Nevertheless, the reaction regime described here finds particular application and offers particular benefits to the assessment of glucose concentration in blood and other body fluids and the methods of doing so described in this application have not previously been described. The invention is not to be limited to the particular regime described herein unless the context dictates otherwise. Thus, the following description is by way of example only, but is nevertheless a preferred way of carrying out the invention.

Figure 2:
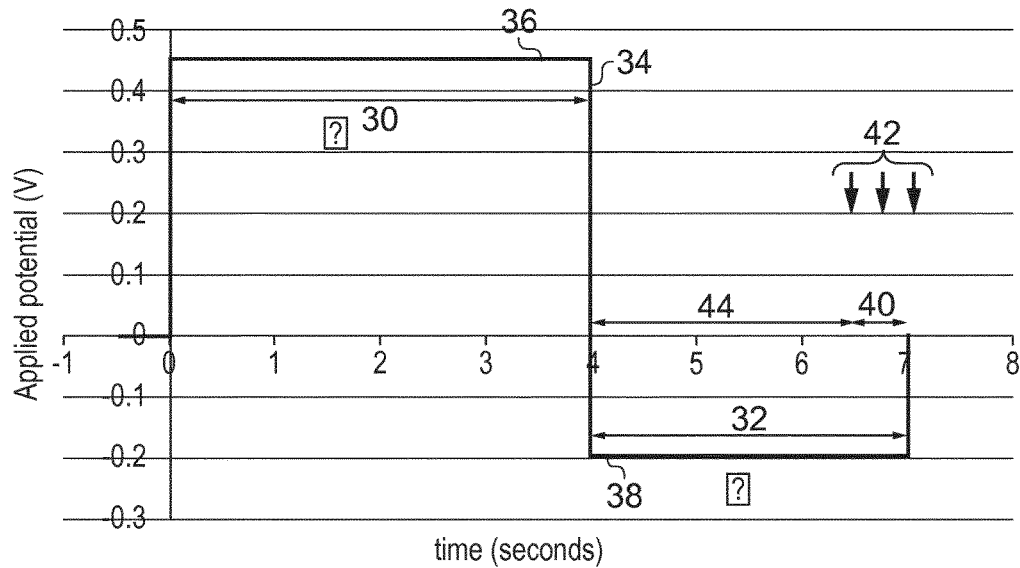
FIG. 2 illustrates the applied potential over time applied between a first working electrode and first counter electrode(s). In this example embodiment, a first time period is 4 seconds long, and a second time period is 3 seconds long.

FIG. 2 shows the potential to be applied over time between working electrode 18 and counter electrode 20 as shown in FIG. 1A. As will be described later, a similar method may be applied to first working and first counter electrodes 18A, 20A of FIG. 1B and preferably also to second working and second counter electrodes 18B and 20B which are not provided with enzyme.

Thus, during a first time period 30, working electrode 18 is at first voltage 36 (here, an oxidising potential of +450 mV) with respect to counter electrode 20. After a predetermined first time period 30 (here 4 seconds), the applied voltage reverses at time 34, so that the working electrode 18 is at a second voltage 38, opposite to the first voltage (here a reducing potential at −200 mV) with respect to counter electrode 20. The working electrode 18 is held at the second voltage 38 for a predetermined second time period 32 (here 3 seconds). One or more measurements are taken during a predetermined time period, here a third time period 40. The third time period 40 is preferably at the end of the second time period.

In some previous prior art methods, the current developed at the working electrode at the end of a period of time, e.g. 5 seconds, may be measured and is related to the concentration of analyte, e.g. glucose, in the fluid sample, e.g. blood. The present method proposes determining a reaction parameter indicative of the concentration of reduced mediator at the counter electrode 20, and preferably indicative of the concentration of reduced mediator after the start of the second time period when the reverse potential is applied. Preferably the reaction parameter is determined from one or more measurements made typically during a third time period 40 at or near the end of the second time period 32. Embodiments of the present method propose measuring a measurement parameter preferably during the third time period 40 e.g. at one or more time points during third time period 40, e.g. at time points 42 within the third time period, or more preferably measuring a measurement parameter over one or more sub-periods within the third time period 40. Optionally, the measurement parameter is measured during a sequence of sub-periods covering all the third time period (the sub-time periods being substantially contiguous one after the other). Optionally, the measurement parameter is measured continuously over the third time period. Optionally, measurements of the measurement parameter e.g. current may be made not only during the third time period but also before the third time period starts so that, for example, the reaction parameter may be determined by calculating the difference between the total charge passed up to the start of the third time period and the total charge passed up to the end of the third time period.

In an example embodiment of the method of the present invention, the reaction parameter is the charge passed via the counter electrode, which is the same as that passed via the working electrode, as measured during the third time period. Typically, the third time period begins after a delay 44 after commencement of the second time period 32. Preferably the third time period ends at substantially the same time as the second time period.

A measurement parameter (e.g. current over time) may be measured to facilitate determination of a reaction parameter (e.g. charge) or a measurement parameter (e.g. current) may be used directly as a reaction parameter indicative of the concentration of reduced mediator at the counter electrode. Where the measurement parameter is a current, it may be a measurement of current at a point in time or measurement of a current over one or more sub-time periods, or measurement of current over the entire third period or measurement over not only the third time period but also before the third time period starts so that, for example, by calculating a difference between the start and the end of the third time period, the reaction parameter e.g. charge, for the third time period can be determined. Nevertheless, in example embodiments it is preferred that the measurement parameter is of the current over a period of time, e.g. current over the third time period (which may be of duration of about ½ seconds), or current over one or more shorter sub time periods (e.g. which may be of duration of about 0.05-0.2 seconds, or more preferably about 0.1 seconds) within the third time period.

Figure 3:
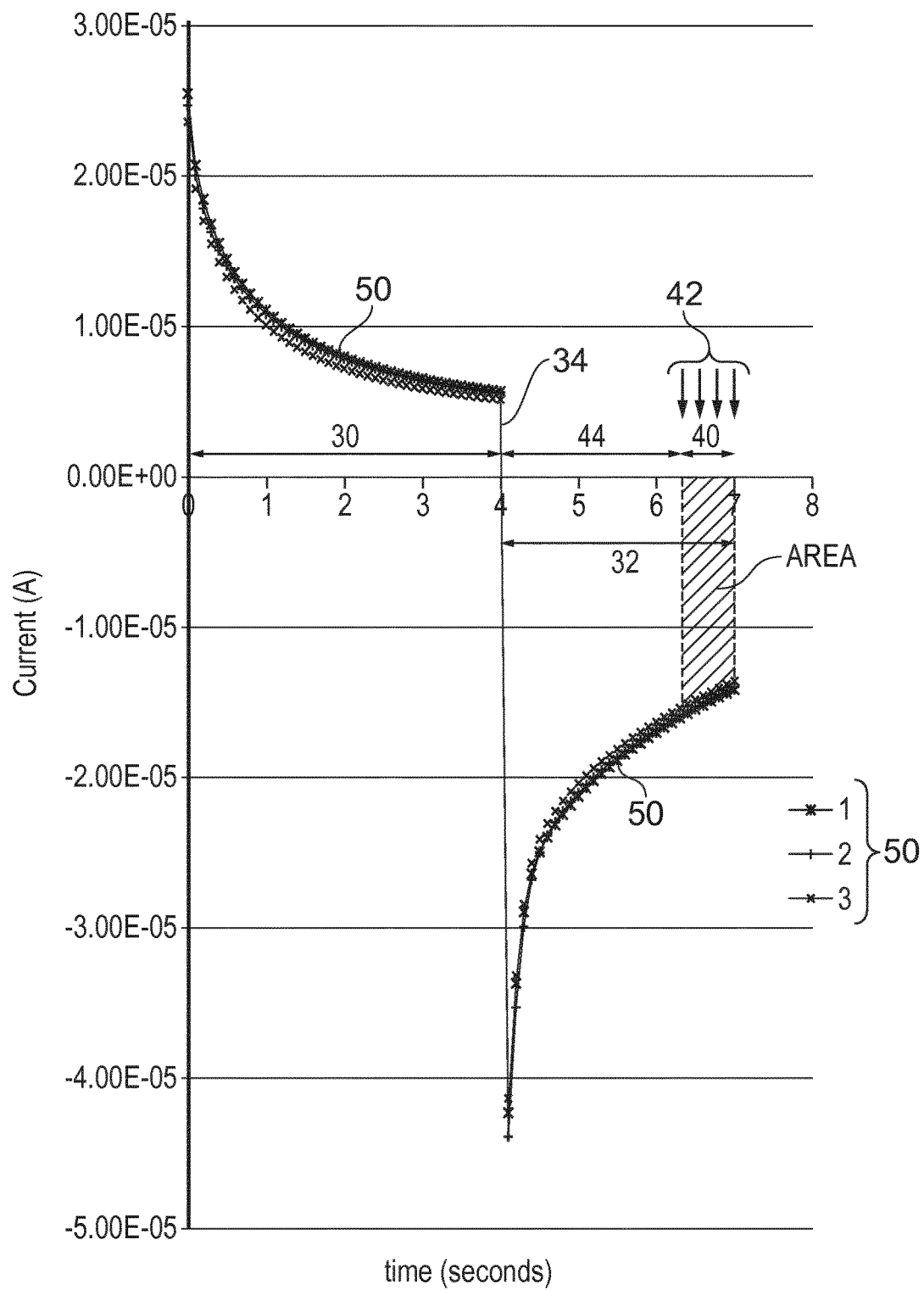
FIG. 3 shows real current transients over time in a working electrode/counter electrode(s) sensor device such as those in FIG. 1A taken at 566 mg/dL glucose, 47% hct in whole blood, and repeated three times, showing small variation between repeats.

In example embodiments, it is further preferred that the reaction parameter is charge passed during the third time period, or charge passed during one or more shorter sub-periods within the third time period, charge being equal to (current)×(time). Thus, in current transient curves shown in FIGS. 3 and 5, the reaction parameter is the charge passed which may be determined from the area under the current transient curve during the third time period 40 or the area under the current transient curve during a number of sub-periods, each sub-period commencing, for example, at time points 42. Alternatively, preferably the reaction parameter is determined by calculating the difference between the total charge passed up to the start of the third time period and the total charge passed up to the end of the third time period and/or by calculating the total charge passed during the third time period from charge passed during two or more sub-periods each comprising a portion of the third time period and as a whole comprising substantially all the third time period.

Figure 13:
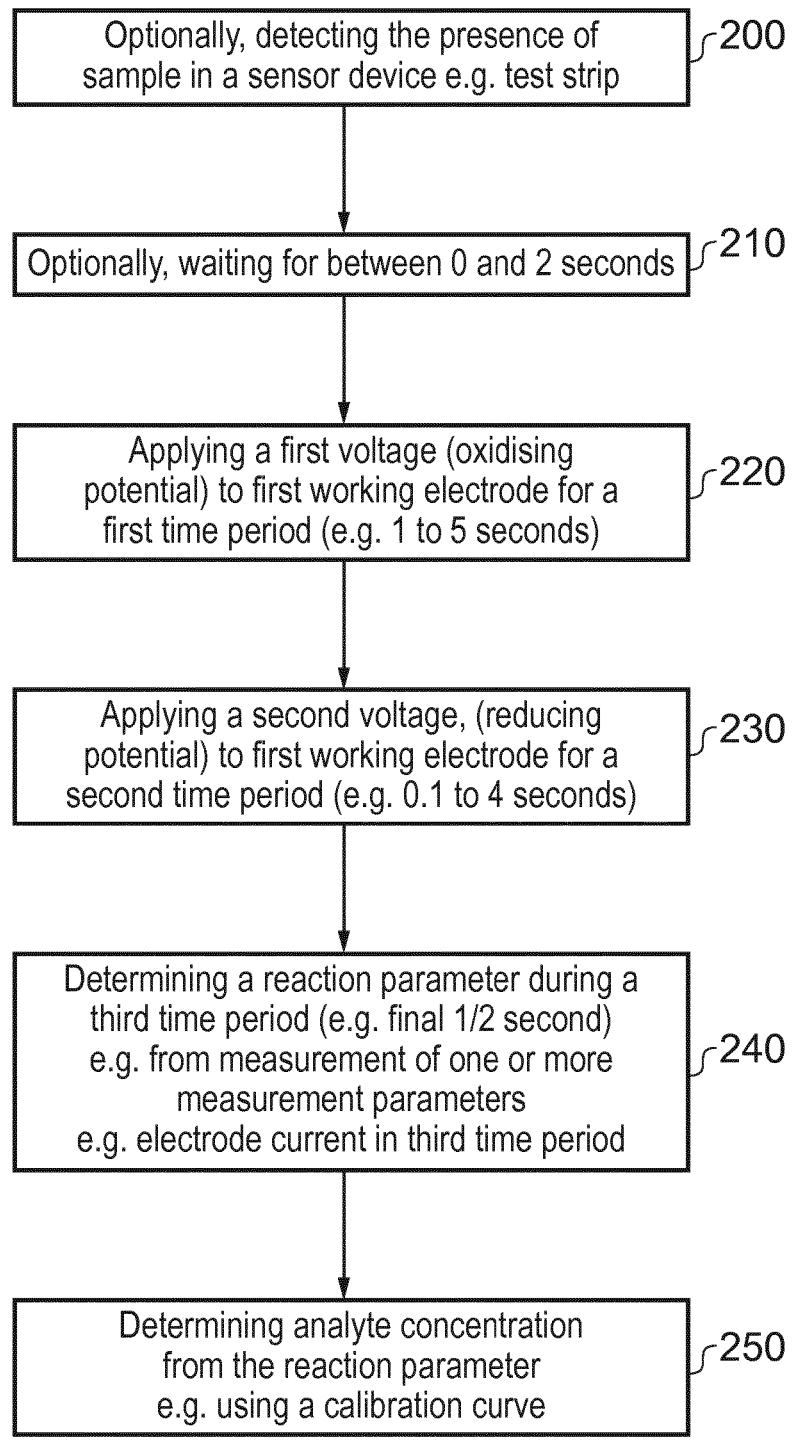
FIG. 13 shows method steps of a method according to a first example embodiment of the invention, for example, for use with the sensor device of FIG. 1A.

Referring briefly to FIG. 13, in step 200, optionally, the presence of sample in the test sensor device 10 is carried out, e.g. using a fill detect electrode or pair of electrodes, as understood by someone skilled in the art. In step 210, optionally a preliminary time period of up to about 2 seconds may be allowed to elapse prior to commencing the voltage sequence. In step 220, a first voltage (oxidising potential) 36 is applied during a first time period 30 to first working electrode 18 (see FIGS. 1A and 2). In step 230, a second voltage (reducing potential) 38 is applied during a second time period 32 typically commencing immediately after the end of the first time period. In step 240, a measurement parameter is determined during a predetermined time period which here is a third time period 40 (see FIG. 2). The third time period 40 commences after a delay 44, some time after the commencement of the second time period. Delay 44 may be about 0.1 to about 5 seconds, or preferably about 1 to about 3 seconds, or more preferably about 1 to about 2 seconds. During this third time period 40, a measurement parameter such as current over substantially the whole third time period, or over one or more sub-time periods within the third time period 40, may be measured. Typically, current measured during the third time period 32 (the measurement parameter) is converted into the charge passed through the counter electrode 20 to the working electrode 18 during the third time period 40, this amount of charge passed during this time period being the reaction parameter.

It will be understood by those skilled in the art that a reaction parameter e.g. such as charge passed, e.g. during the third time period, may be measured and/or calculated from measurements e.g. such as current, in a number of different ways. In practice, such variations in charge calculation methods, produce little significant variation in the total charge passed during the predetermined time period, here the third time period. It will also be understood by those skilled in the art that measurements (e.g. of current) may be made so as to determine the difference between total charge passed up to start of the third period and total charge passed up to the end of the third period which is then representative of the third period only and indeed can be used to provide a reaction parameter indicative of the concentration of reduced mediator at the counter electrode for the third period, which commences after the second time period starts and preferably ends at the same time.

In one example embodiment, the measurement parameter, such as current, may be measured at a series of time points 42, or more preferably during a series of sub-periods within third time period 40, to provide a series of measurements. This may be a series of instantaneous current measurements at the working and/or counter electrode. This may be a series of quasi-instantaneous charge measurements, such as the charge passed during a shorter sub-period of, for example about 0.01 seconds to about 0.5 seconds or more preferably about 0.1 seconds, within the third time period. These measurements of charge during sub-periods of time within the third time period may be used as the reaction parameter (see cumulative charge measurements 66 in FIG. 6). For example, the cumulative charge determined at the end of the third time period, may be the reaction parameter which is used as the response of the sensor device from which glucose concentration can be calculated using a calibration curve.

A reaction parameter may be measured directly or determined from one or more measurement parameters. Preferably if a measurement parameter or series of measurements parameter(s), such as current over the third time period, has been measured these are used to determine a reaction parameter. For example, measurement parameter(s) of current are converted into cumulative charge passed during a predetermined time period, here the third time period, and this is used as the reaction parameter(s). In step 250 the reaction parameter(s) is used to calculate the analyte concentration, e.g. using a calibration curve such as that seen in FIGS. 4, 8 and 10.

Turning back now to FIG. 3, three current transients 50 are shown. The three repetitions from three separate sensor devices show good consistency and repeatability at response in sensor devices used with 566 mg/dL glucose in whole blood of 47% Hct.

Figure 4:
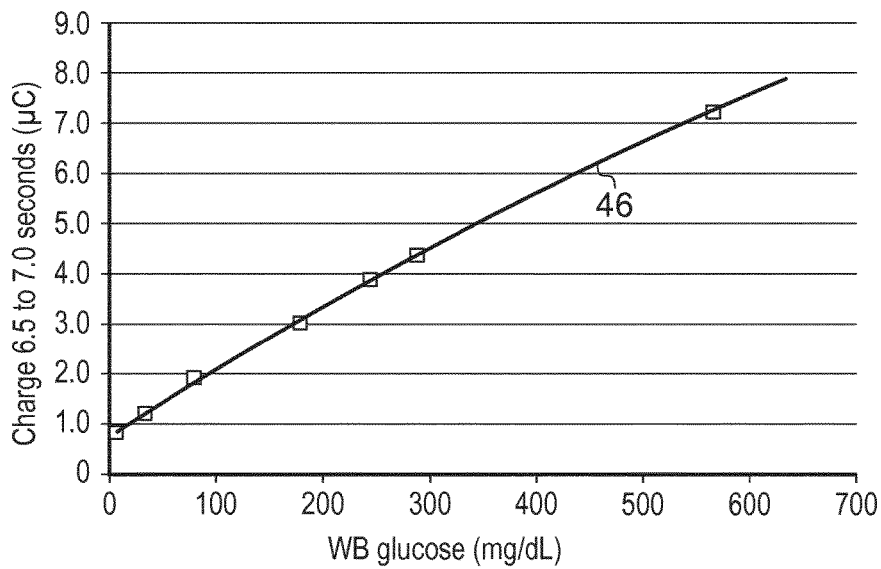
FIG. 4 shows a calibration plot of a reaction parameter measured during a third time period (e.g. total charge passed between e.g. 6.5 and 7 seconds) showing the response of the reaction parameter as a function of whole blood glucose. A near linear response of the reaction parameter is seen.
Figure 5:
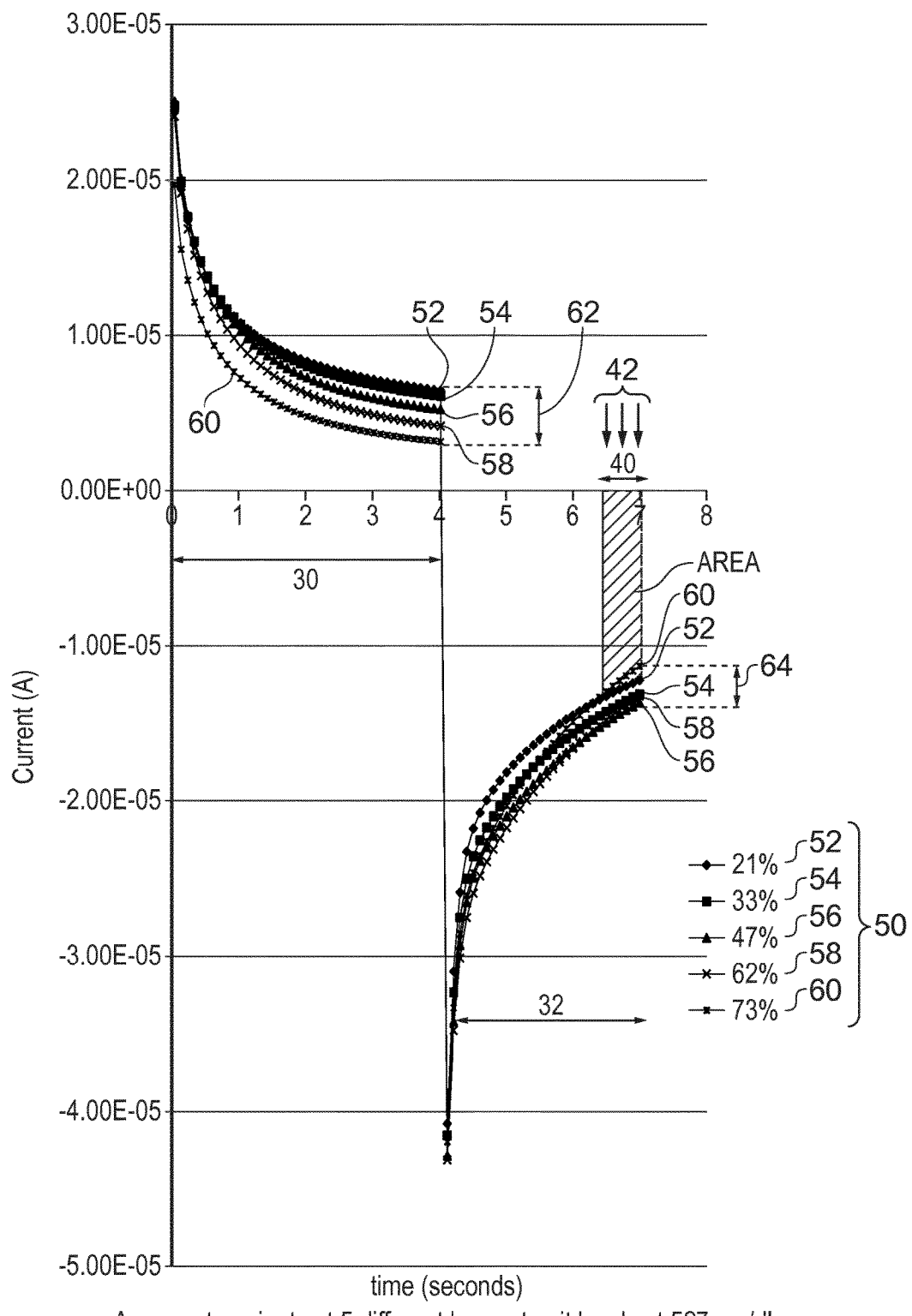
FIG. 5 shows a plot of average current transients versus time, using sensor devices as shown in FIG. 1A and potentials as shown in FIG. 2, from four replicates at each of five different haematocrit levels (21%, 33%, 47%, 62% and 73%) at a glucose concentration of 527 mg/dL in whole blood.

Referring to FIG. 4, a reaction parameter comprising the total charge passing during a third time period 40 as a function of whole blood glucose concentration in a two electrode system (see FIG. 1A) is shown. The third time period 40 during which measurements are taken to determine a reaction parameter, is of duration equal (within expected tolerances) to the last half second of a second time period of 3 seconds (see FIG. 2), FIG. 5 shows five current transients over time (averaged over four repetitions) using the voltage regime of FIG. 2 in sensor devices having the two electrode system of FIG. 1A. The relatively wide spread 62 across the current measurements 52, 54, 56, 58, 60 at different levels of haematocrit at the end of the first time period 30 of 4 seconds shows the dependence of current measurement at 4 to 5 seconds on haematocrit, this being the response used in some prior art methods. The spread 64 of the current at the end of the second (and third) time periods is smaller than spread 62 despite the wide haematocrit range.

Figure 6:
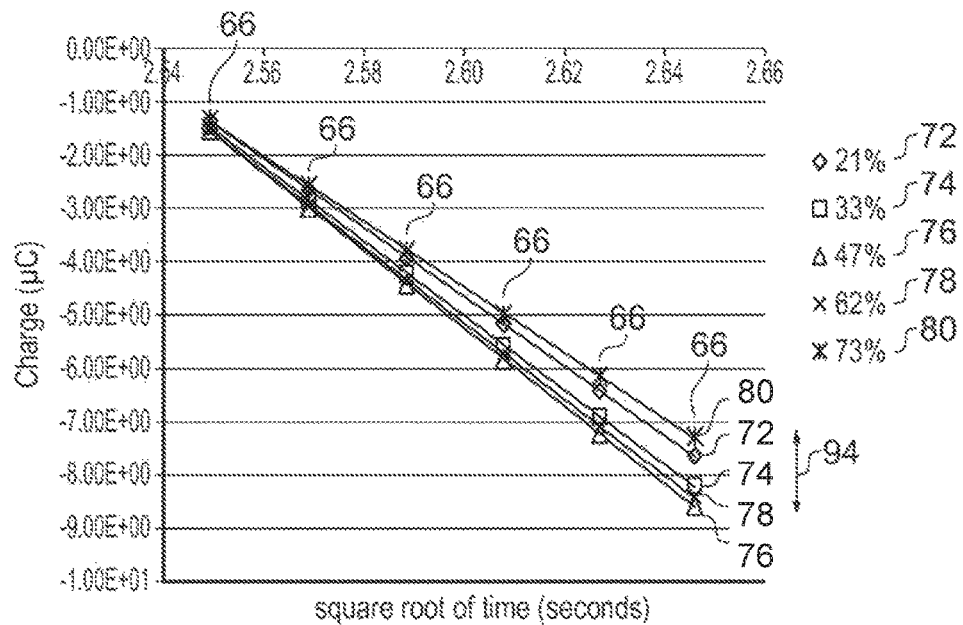
FIG. 6 shows a plot of a reaction parameter according to a method of the invention. Here the reaction parameter is total charge passed during various sub-periods within or over a third time period (here between 6.5 and 7.0 seconds), the third time period comprising the last portion of a second time period, versus the square root of time at each of the five different haematocrit levels (21%, 33%, 47%, 62% and 73%). Thus, at 6.5 seconds the current transient is measured for a sub-period of 0.1 seconds. The total charge passed during this period of current flow is determined (e.g. =average current measured×sub-period e.g. 0.1 seconds) and then cumulative charge, i.e. charge over that time period and all preceding time periods since 6.5 seconds, is plotted against the square root of time.

Referring now to FIG. 6, this shows the cumulative charge passed during six sub-periods of 0.1 second each, the sub-periods being contiguous between 6.5 and 7.0 seconds. Thus, current was measured at 6.5 seconds for a sub-period of 0.1 seconds and immediately thereafter at 6.6 seconds for a sub-period of 0.1 seconds and so on. The sub-period may vary depending on the sampling rate and may, for example, be about 0.01 seconds to about 0.5 seconds (within expected tolerances).

The measurement parameters of current are converted to charge by multiplying the current by the duration of the sub-time period (e.g. 0.1 seconds). The cumulative charge in micro coulombs, C is plotted against the square root of time and shows a linear increase, such that at the end of the third time period, here 7 seconds (2.65 on the X axis in FIG. 6), a total charge passed during the third time period can be determined from the Y axis. This quantity may be used as the reaction parameter.

As an aside, plotting the data as in FIG. 6 is optional, but it is illustrative of the measurement of the accumulated charge passed during the predetermined third time period 40. There is a small spread 94 in the reaction parameter (here, accumulated charge at 7 seconds) for each of the lines 72, 74, 76, 78, 80 representing total charge passed during the third time period at haematocrits 21%, 33%, 47%, 62%, 73% respectively.

Figure 7:
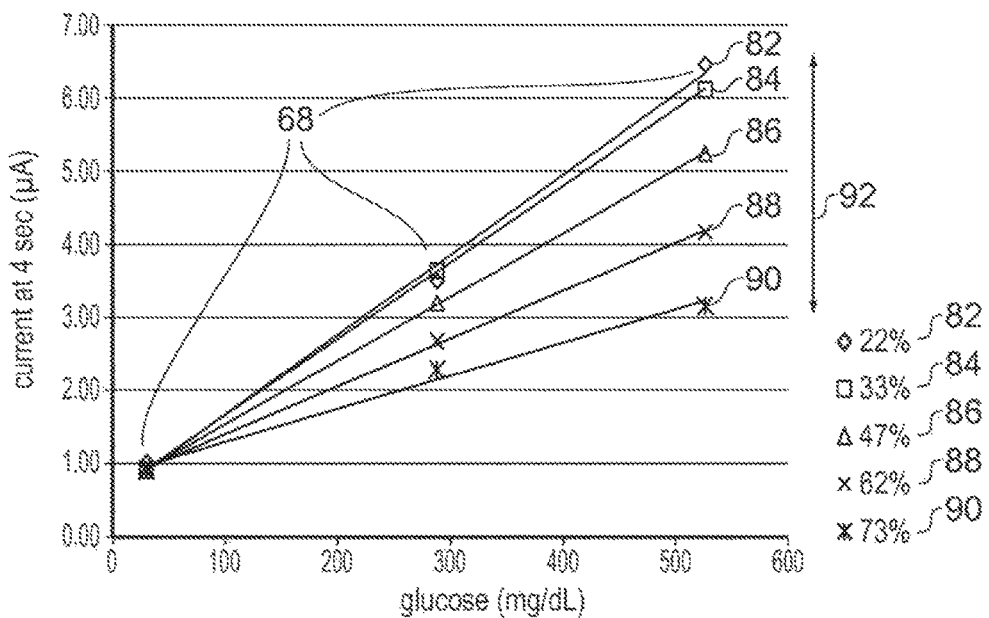
FIG. 7 shows a calibration curve constructed from real data and reflective of prior art methods, showing the current measured at 4 seconds versus glucose concentration in the fluid sample at each of the five different haematocrit levels.
Figure 8:
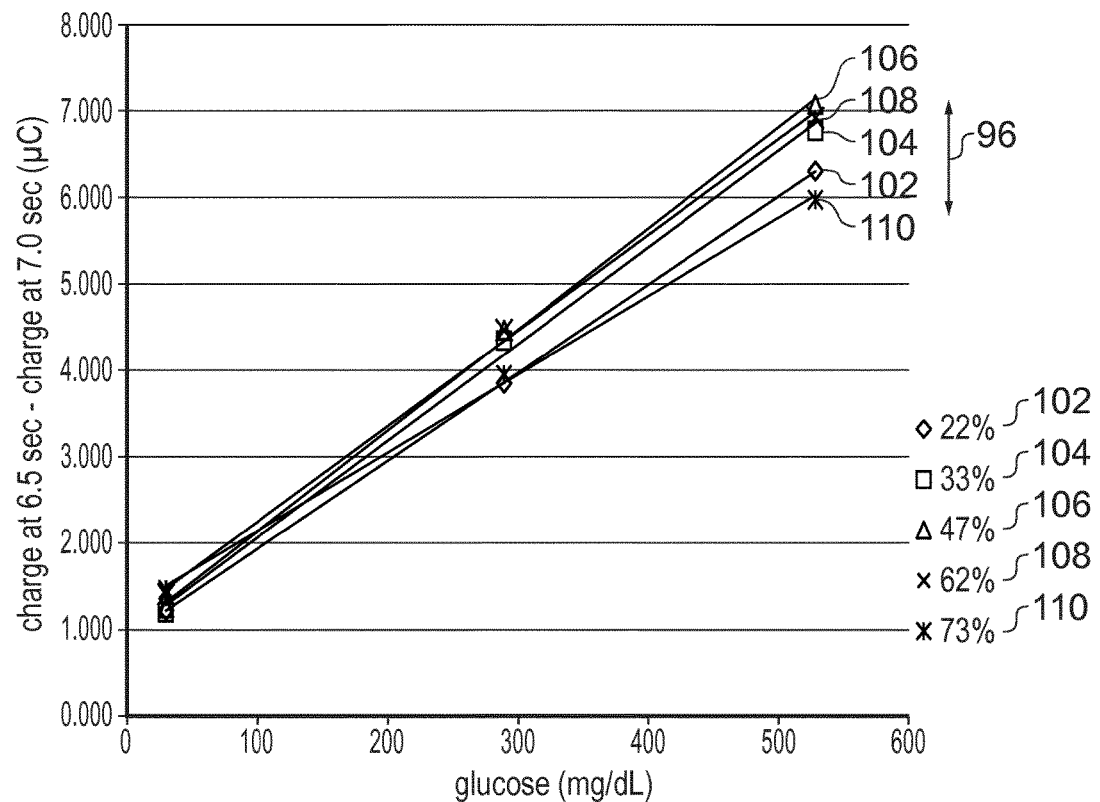
FIG. 8 shows a calibration curve constructed from real data illustrating results achievable with the methods of the present invention in which a reaction parameter (for example, total charge passed between, for example, 6.5 and 7.0 seconds) is measured versus glucose concentration in the fluid sample at each of the five different haematocrit levels.

FIG. 7 illustrates the calibration curves obtainable by some prior art methods (measuring current at 4 to 5 seconds)

and FIG. 8 illustrates calibration curves obtainable by one or more methods of the present invention. In the present case, data in FIG. 8 were obtained by measuring total charge passed during a third time period, commencing after the start of the second time period, for a range of glucose levels and haematocrit levels.

At higher glucose and higher haematocrit a spread is seen in both FIGS. 7 and 8. The spread 92 in the response (here current) at highest glucose and highest haematocrit in FIG. 7 is a relatively large variation as a percentage of the measurement and may more easily result in inaccurate glucose concentration results. In FIG. 8 the response is the reaction parameter which is cumulative charge in the last half second of a 3 second, second time period 32. The spread 96 in the response (here total charge) in FIG. 8 at highest glucose and highest haematocrit as a percentage of overall measurement is less than that seen in FIG. 7.

Figure 9:
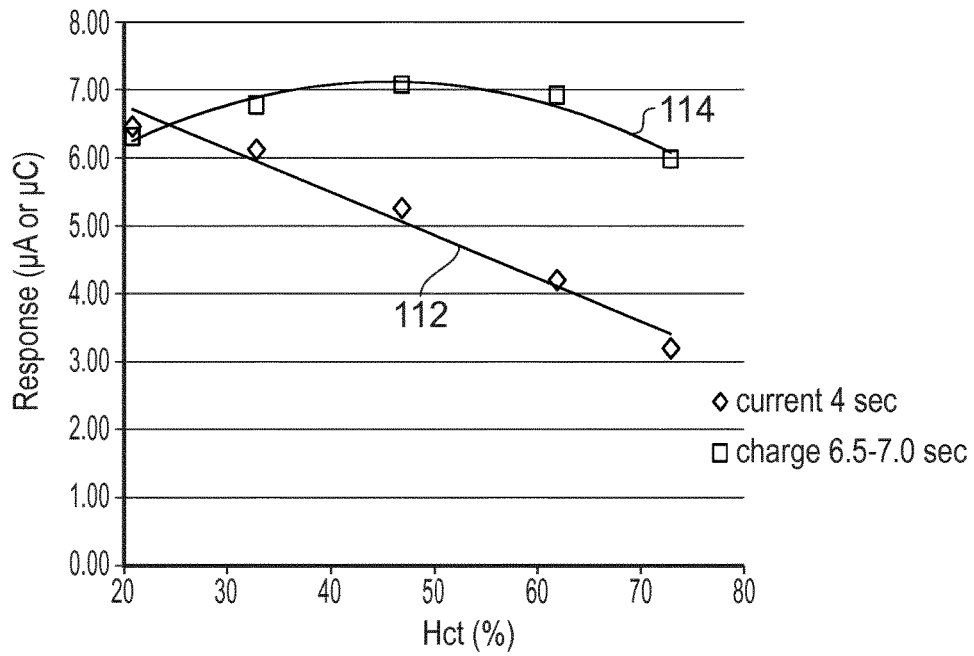
FIG. 9 shows the response of two response parameters, firstly, current measured at 4 seconds and, secondly, a reaction parameter according to a method of the invention (here, a charge passed during a third time period, which here is 6.5 to 7.0 seconds), plotted versus haematocrit level. The results were taken at high haematocrit using 527 mg/dL in whole blood and the average of four replicates is shown.

This can be seen more clearly in FIG. 9 in which the average response (either current at 4 seconds, or total charge passed in the third time period) at high glucose as a function of haematocrit is shown. The response 112 of current at 4 seconds varies considerably with variation in haematocrit, falling from around 6.5 to around 3 between 21% and 73% haematocrit. The response 114 of charge between 6.5 and 7.0 seconds varies much less between around 6 or just over 7 between 21% and 73% haematocrit and in the central haematocrit range of 30% to 60% is almost linear (values hovering around 7).

Whilst a first time period of 4 seconds, a second time period of 3 seconds and a third time period of ½ second ending at the same time as the second time period are described, other time periods may be used as outlined elsewhere herein. As a further example, FIG. 10 illustrates a calibration curve 146 obtained from two electrode sensor devices such as those in FIG. 1A using an applied potential of +450 mV for a first time period 30 of 3 seconds (phase 1) and an applied potential of −200 mV for a second time period 32 of 2 seconds (phase 2), the sensor device response here uses the reaction parameter of charge in µC passed during the last half second (third time period 40) of the second time period 32.

Figure 10:
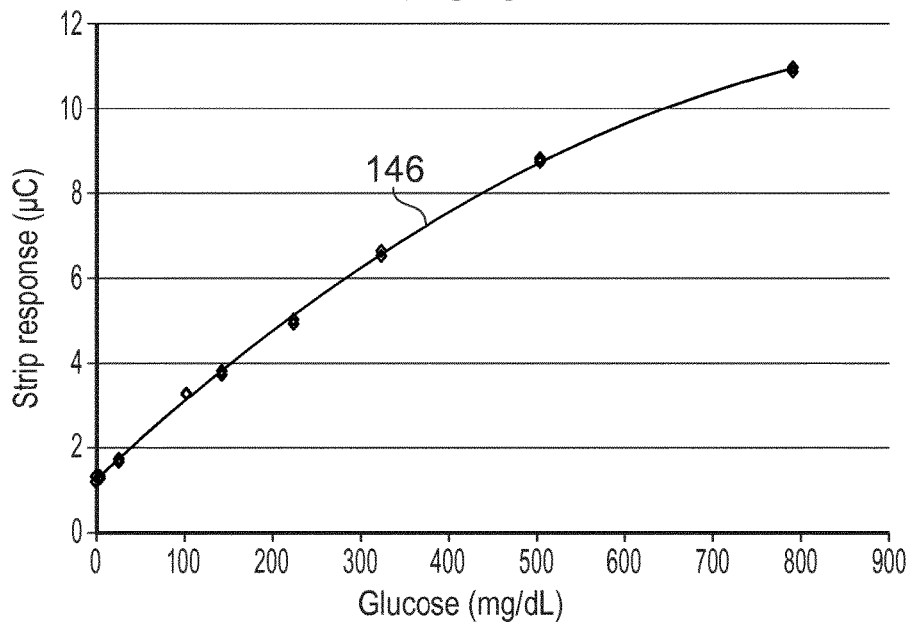
FIG. 10 shows a calibration curve, similar to that seen in FIG. 4, illustrating a sensor device response according to method(s) of the invention. Here, the response is the reaction parameter measured according to one or more methods of the invention. In this case, the reaction parameter is charge passed in a third time period, here the last half second of the second time period) versus glucose concentration, the first time period being three seconds long, the second time period being two seconds long.
Figure 11:
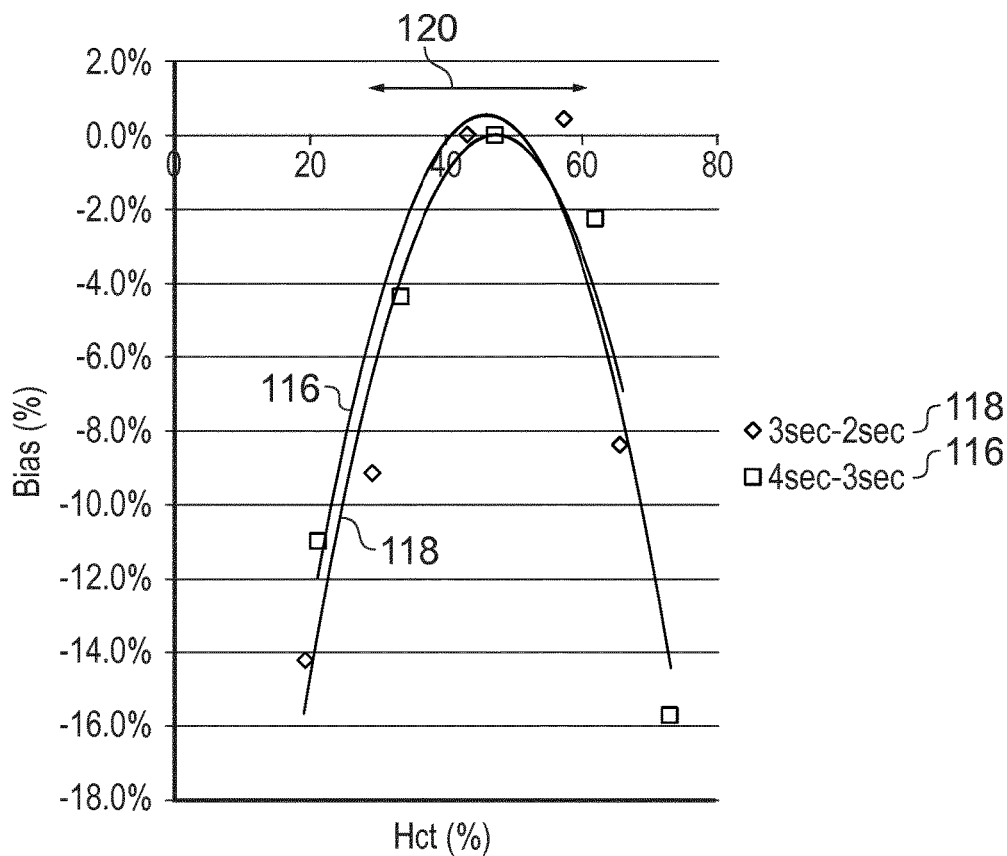
FIG. 11 shows the bias of the response (here the response being the reaction parameter of charge measured during a third time period of half a second falling during the last half second of the second time period) away from the comparable response at 42% haematocrit, for the five different haematocrit levels (21%, 33%, 42%, 62%, 73%) for two different combinations of first and second time periods (first time period of 3 seconds, second time period of 2 seconds—diamonds 118, and first time period of 4 seconds, second time period of 3 seconds—squares 116).

A comparison of the variation of the response of the sensor (in other words variation in the reaction parameter) as a percentage away from the response at 42% hct in high glucose (520 mg/dL) whole blood, is illustrated in FIG. 11 for the two different assay timing regimes of FIG. 2 (4 seconds, 3 seconds) and FIG. 10 (3 seconds, 2 seconds). This shows that between haematocrit levels at 30-60% both assay timing regimes result in a bias of less than around 4-5%. This reduction in the variation across this central haematocrit range represents a considerable improvement over prior art methods.

Figure 12:
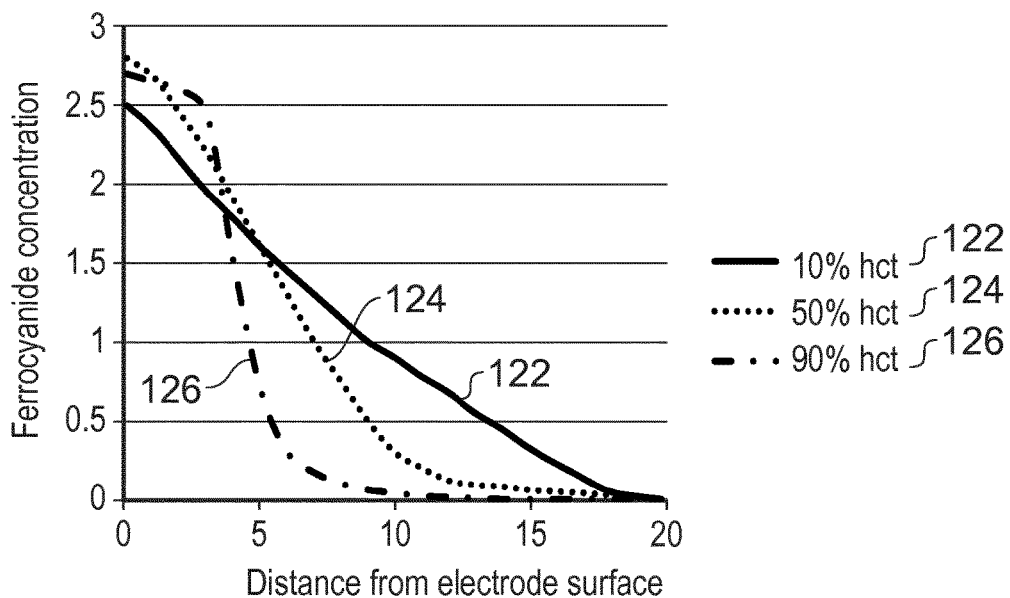
FIG. 12 shows an illustrative plot of expected reduced mediator (here ferrocyanide) concentration gradient at the counter electrode at the end of the first time period also known as (phase 1) for different haematocrit levels, the concentration gradients at 10% hct, 50% hct and 90% hct being labelled 122, 124 and 126 respectively.

Referring now to FIG. 12, this is an illustrative plot showing the anticipated ferrocyanide concentration gradients at the counter electrode 20 at the end of the first time period. After commencement of the second time period, the ferrocyanide close to the counter electrode is measured during a relatively short third time period and relatively soon after the second time period commences.

Figure 14:
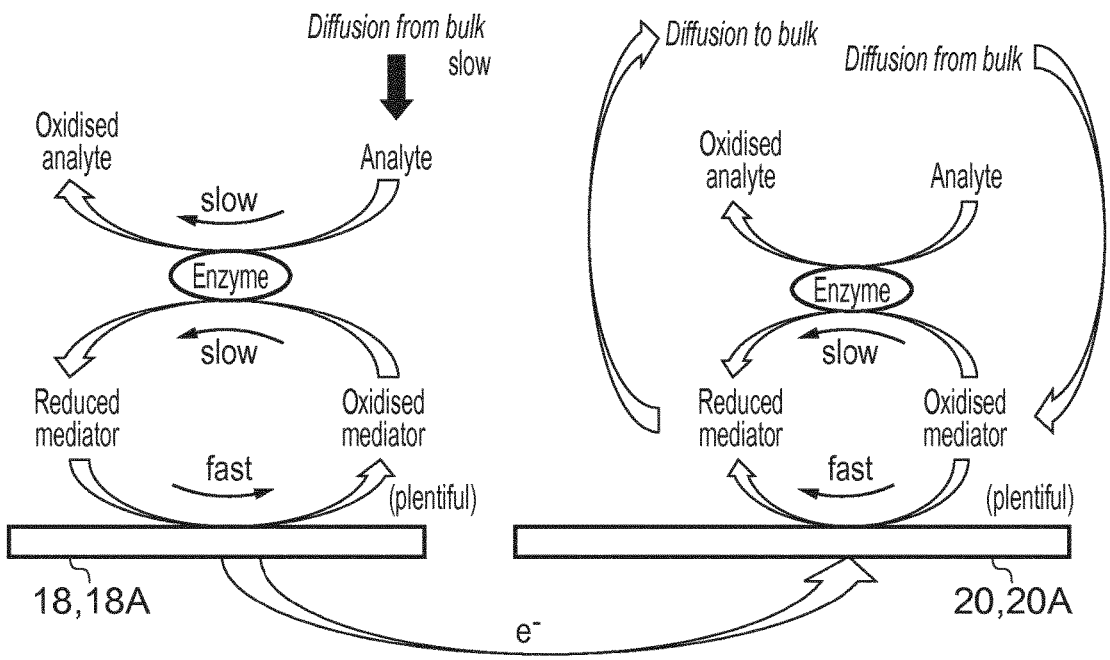
FIG. 14 shows a schematic illustration of the reaction regime in the first time period (Phase 1) and in the second time period (Phase 2) in a two electrode system such as that shown in FIG. 1A. The invention may be used with alternative electrochemical mediated redox reaction schemes other than the one illustrated, as would be understood by someone skilled in the art from the information disclosed in the present application.
Figure 14:
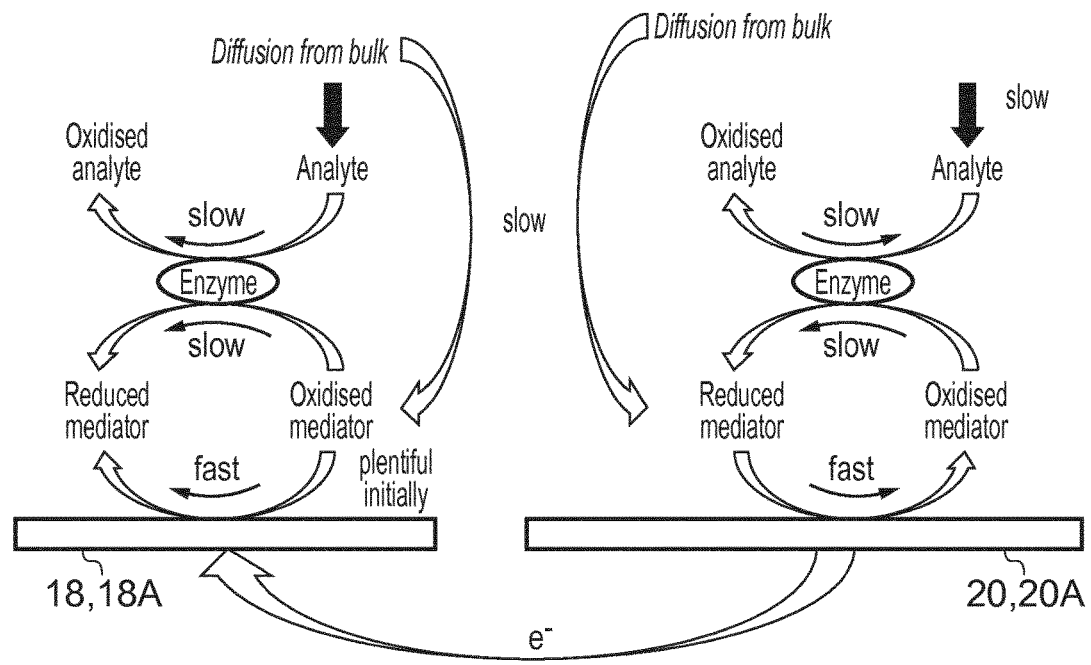

Referring now to FIG. 14, an example of a redox reaction suitable for use in methods of the present invention is shown. Other mediated redox reactions may be used, with suitable adjustment of voltages, sensor device design and/or duration of first, second and third time periods.

Figure 15:
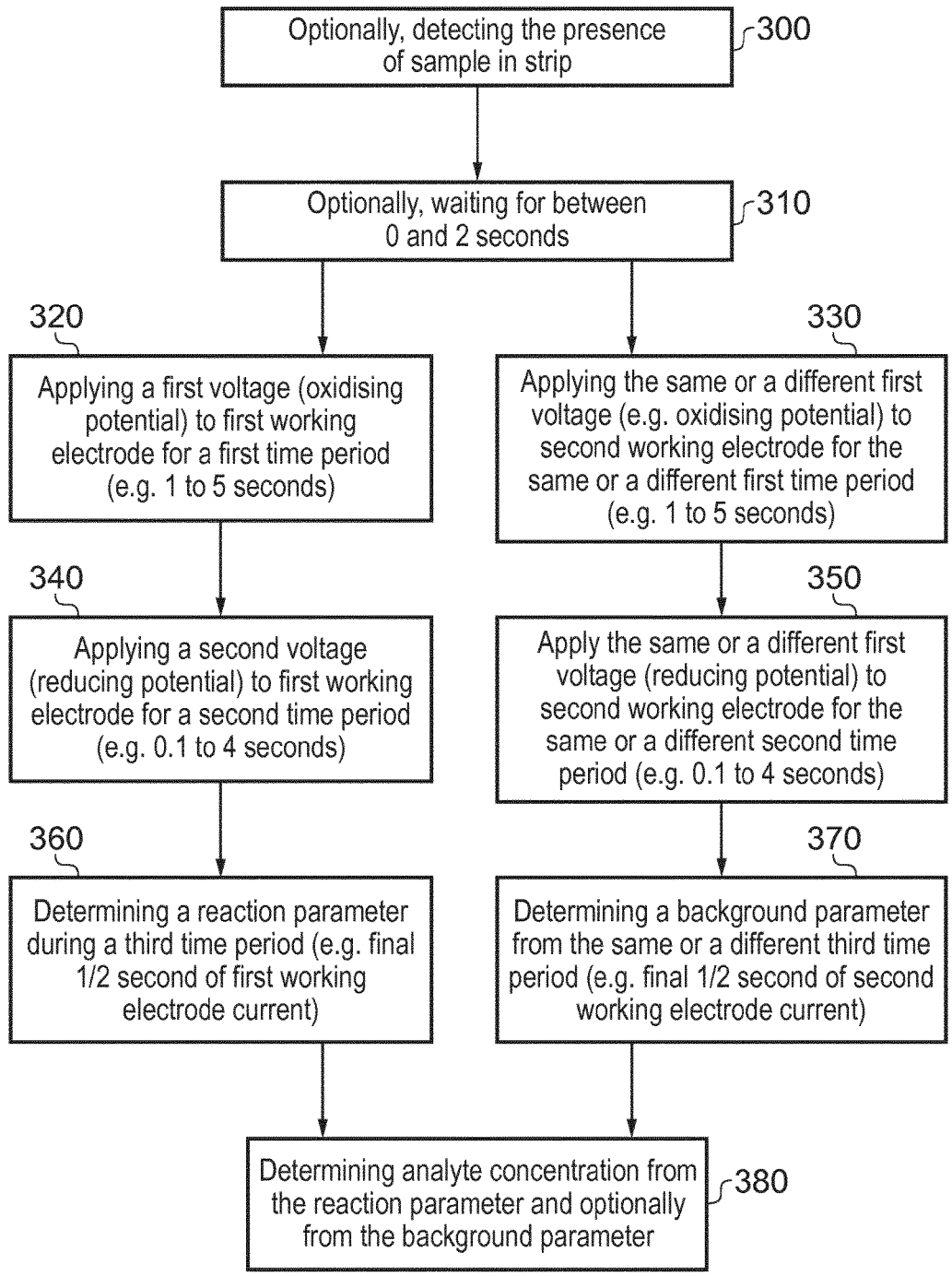
FIG. 15 shows method steps of a method according to a further example embodiment of the invention, for example, for use with the sensor device of FIG. 1B, to introduce a background error correction.

In FIG. 15, an example method of the invention incorporating a background correction using background electrodes such as those shown in FIG. 1B are shown. In step 300 optionally the presence of a sample is detected, optionally, a delay of 0 to 2 seconds is provided before applying potentials to the system. In step 320 a first voltage (preferably an oxidising potential) is applied to the first working electrode 18A for a first time period 30 and in step 330, preferably the same (or a different) first voltage is applied to the second working electrode 18B for preferably the same (or a different) first time period 30. In step 340 a second voltage (preferably a reducing potential) is applied to the first working electrode 18A for a second time period 32 and in step 350, preferably the same (or a different) second voltage is applied to the second working electrode 18B for preferably the same (or a different) second time period 32. In step 360, a reaction parameter (e.g. charge passed in a time period) is determined from one or more measurement parameters (e.g. current) preferably measured during a third time period 40. In step 370, a background parameter is determined from one or more measurement parameters measured for preferably the same (or a different) third time period 40. Finally, in step 380, analyte concentration is determined from the reaction parameter (e.g. charge passed in a time period) and preferably is corrected by using the background parameter as a correction factor/amount.

In summary, the method(s) of the invention is an electrochemical method using the well established mediated enzyme principle. Two different voltages are applied between the working and counter electrodes. The first potential is one that will oxidise the reduced form of the mediator generated by reaction of the enzyme with glucose. The second potential, applied immediately after the first, is a potential that will reduce the mediator directly at the working electrode. The first phase of the assay (when the first potential is applied) may last for approximately 4 seconds and the second phase (when the second potential is applied) may last for approximately 3 seconds. With appropriate assay timings, electrode areas and reagent composition, a measurement of the charge passed in e.g. the final ½ second of the second phase of the assay is proportional to the sample glucose concentration and substantially less influenced by the sample haematocrit than just measuring the current 5 seconds after the application of a single oxidising potential for example.

A background measurement pair of electrodes covered with a reagent film containing mediator but no enzyme may be used to subtract a background response and eliminate interference from ascorbate, uric acid or other interferent for example.

Electrodes are preferably screen printed carbon. The reagent film contains Glucose Dehydrogenase—FAD and ferricyanide plus other non-reactive components and may be applied as a thin dry film. The current at 4 seconds is dependent on haematocrit level as would be anticipated. A plot of the charge passed between 6.5 seconds and 7 seconds for all 5 transients is shown in FIG. 6. The x-axis uses the square root of time as a plot of charge vs sqrt time is linear. The calibration curves for the different haematocrit levels when using the current at 4 seconds as the response are shown in FIG. 7. FIG. 8 are the same curves but using the charge difference between 6.5 seconds and 7.0 seconds as the response. If the response from different haematocrit samples at just 527 mg/dL glucose is plotted then a further benefit of the novel method can be seen. FIG. 9 shows that instead of being a linear effect, the effect of haematocrit between 33% and 62% (where most samples will occur) is very little and the response decreases at even higher and lower haematocrit levels. The assay method can also use different timings for the phases of the assay. For example FIG. 10 illustrates the calibration curve obtained using a 3 second phase 1 followed by a 2 second phase 2:

Without wishing to be bound by theory, the following is a possible explanation as to why a reaction parameter determined during the second time period, e.g. over a third time period, is indicative of the concentration of analyte in the sample. In phase 1 initially there is high concentration of mediator, here ferricyanide, over both working electrode 18 and counter electrode 20. Also enzyme, here GDH, is present on both.

As a brief aside, in the right hand side of the method illustrated in relation of FIG. 15 as used with a sensor device 10 such as that shown in FIG. 1B, the second working and second counter electrodes 18B and 20B have mediator but not enzyme on these at the start of phase 1. The following possible explanation may equally apply to the first working and counter electrodes 18A, 20A and even to the second working and counter electrodes 18B, 20B operating as background electrodes with commensurate changes to reflect the absence of active enzyme on the second working and counter electrodes 18B, 20B.

Continuing with the possible explanation, in the first time period 30 (phase 1), initially at the working electrode 18, the relatively slow enzyme reaction proceeds converting glucose which is diffusing in from the bulk towards the electrode. The diffusion in of glucose is also relatively even slower and haematocrit dependent, the diffusion rate being dependent upon the haematocrit concentration in the fluid sample. The enzyme (GDH) similarly reduces oxidised mediator (ferricyanide) to reduced mediator (ferrocyanide) but also relatively slowly. The reduced mediator (ferrocyanide) is immediately and quickly oxidised at the electrode surface, thus the oxidised mediator is recycled and is in plentiful supply. The overall reaction at the working electrode 18 is determined by the availability of glucose which depends on diffusion of glucose from the bulk, and this is haematocrit dependent.

At the counter electrode in phase 1, analyte (here glucose) is oxidised by the enzyme (as at the working electrode), and oxidised mediator (ferricyanide) is reduced to ferrocyanide (this is the first process producing ferrocyanide at the counter electrode). At the same time, as soon as an electron is made available (by flow of electrons from working electrode 18 to counter electrode 20) the plentiful oxidised mediator (ferricyanide) is reduced at the counter electrode surface to reduced mediator (ferrocyanide). This is the second process producing ferrocyanide at the counter electrode 20. Both the first and the second processes producing ferrocyanide at the counter electrode result from oxidation of analyte by enzyme, one happening at the counter electrode (process 1) and one happening at the working electrode (process 2). Thus, the availability of ferrocyanide at the counter electrode from the second process is dependent on electron flow (current) from the working electrode and therefore is dependent on the rate of reaction happening at the working electrode which itself depends on the ability of glucose analyte to diffuse in from the bulk.

In the second time period (phase 2), the enzyme oxidation of analyte continues at working electrode 18 and at the counter electrode 20. The reduction of initially plentiful oxidised mediator (ferricyanide) begins at the working electrode but is limited by the availability of electrons passed as a current from the counter electrode 20. At the counter electrode, the reduced mediator ferrocyanide is oxidised at the electrode surface to generate the current. Thus, the current generated at the counter electrode 20 is determined by the availability of ferrocyanide in the vicinity of the counter electrode 20. There is a limited supply of ferrocyanide this having been generated during the first time period (phase 1) by process 1 and process 2. Almost immediately after the switch in voltage, the ferrocyanide concentration at the electrode surface drops to near zero, and the diffusion of ferrocyanide to the electrode surface determines the current flow. This ferrocyanide is thought to be reflective of the quantity of glucose producing ferrocyanide in process 1 and process 2; the ferrocyanide produced having diffused away from the counter electrode surface during phase 1. Therefore, the current flowing is limited by the ferrocyanide availability at and near the counter electrode.

By determining a suitable reaction parameter, which may be current over time but is preferably total charge passed during a predetermined third time period, an indication of the available reduced mediator ferrocyanide at the counter electrode surface can be determined. It has been found that a reaction parameter determined according to one or more methods of the invention is proportional to glucose concentration. By use of suitable calibration curve(s) the reaction parameter can be used to calculate analyte (e.g. glucose) concentration.

Under low haematocrit conditions, during the first time period, analyte (e.g. glucose) diffusion is high leading to a higher current flow at the working electrode, (compared to currents at higher haematocrit conditions), however, under low haematocrit conditions during the first time period, diffusion of the reduced mediator (e.g. ferrocyanide) away from the counter electrode is correspondingly high, leading to, it is speculated, a mitigation in the current measured over a predetermined third time period. Thus, in the first time period, at low haematocrit levels, if current flow is higher, more reduced mediator is produced. However, it is speculated during the second time period less reduced mediator is oxidised because it has diffused away more quickly in the first time period producing a commensurate balancing reduction in current flow over a period of time. Under high haematocrit conditions, lower analyte diffusion to the working electrode and lower reduced mediator diffusion away from the counter electrode are thought to occur in phase 1 to produce a similar effect.

To summarise, the possible explanation is as follows: initial conditions at the start of phase 1 are of high ferricyanide over working electrode and counter electrode and enzyme present on both (or neither for background electrode).

During phase 1 (first time period) at the working electrode, GDH oxidises glucose and generates ferrocyanide from ferricyanide; most ferrocyanide is re-oxidised back to ferricyanide at the electrode surface so ferricyanide concentration remains more or less constant. Current becomes glucose diffusion dependent (and therefore haematocrit dependent).

During phase 1 at the counter electrode: GDH oxidises glucose and generates ferrocyanide from ferricyanide. Ferricyanide is converted to ferrocyanide at the electrode surface to balance current developed at the working electrode. As enzyme diffusion is relatively slow ferrocyanide generation is mainly at and near the counter electrode surface. Enzyme reaction rate may be slower than at the working electrode due to depletion of ferricyanide.

The anticipated ferrocyanide concentration gradients at the counter electrode surface at the end of phase 1 are shown in FIG. 12 for three haematocrit levels (distance and concentration units are arbitrary):

As would be expected the total area under the curve is greatest for the 10% haematocrit curve 122 and least for the 90% hct curve 122. However during the short phase 2 only the ferrocyanide close to the electrode is measured. If we look at the areas under the curve within arbitrary unit '5' then the areas are very similar with the 50% curve being slightly larger than the other two as is seen experimentally.

During phase 2 (the second time period), at the working electrode ferricyanide is converted to ferrocyanide and ferricyanide concentration (initially high) drops at electrode surface.

During phase 2, at the counter electrode surface ferrocyanide is converted to ferricyanide. the only ferrocyanide available for this reaction was generated during phase 1 therefore the current flowing is limited by ferrocyanide availability at the counter electrode. The availability of ferrocyanide is determined by diffusion of ferrocyanide away from the electrode surface in phase 1 and to the counter electrode in phase 2 which is dependent on the 'bulk' ferrocyanide concentration.

Under low haematocrit conditions although during phase 1 glucose diffusion is high leading to increased currents, the diffusion of ferrocyanide away from the counter electrode is also high. The two diffusion rates, glucose to the working electrode in phase 1 and ferrocyanide away from the counter electrode in phase 1, are thought to balance, leading to a mitigation of the higher glucose dependent current.

It will be understood that the term 'current' in this disclosure is to be understood in its normal sense in the common general knowledge as the rate of charge flow and is indicative of the rate of reactions occurring in an electrochemical reaction. Similarly, the term 'charge' in this disclosure is to be understood in its normal sense in the common general knowledge as the charge transported by a current in a time period, (in other words number of electrons passed) which in an electrochemical reaction is indicative of the absolute number of reactions occurring (within a time period).

It will be understood by those skilled in the art that various embodiments can be envisaged from the disclosure herein and all such embodiments are intended to lie within the scope of the invention. Accordingly the above description of specific embodiments is made by way of example only and not for the purposes of limitation unless the context dictates otherwise.

The invention claimed is:

1. A method of determining concentration of an analyte in a fluid sample deposited on a sensor device having a working electrode and a counter electrode provided on a substrate, in which the working and counter electrodes are both provided with an enzyme and a mediator for carrying out a mediated redox reaction, the method comprising:
   applying an oxidising potential at a first voltage between the working and counter electrodes during a first time period;
   applying a reducing potential at a second voltage between the working and counter electrodes during a second time period;
   wherein a duration of the first time period is greater than a duration of the second time period;
   determining a reaction parameter, the reaction parameter being indicative of the concentration of reduced mediator at the counter electrode after commencement of the second time period; and
   using the reaction parameter to determine the concentration of analyte.

2. A method according to claim 1 in which a reaction parameter is determined from one or more measurements made only after commencement of the second time period.

3. A method according to claim 1, wherein determining a reaction parameter comprises measuring a measurement parameter comprising one or more measurements.

4. A method according to claim 1, wherein the measurement parameter is a current.

5. A method according to claim 1, wherein the reaction parameter is a charge or a cumulative charge, and wherein the reaction parameter is passed via the working and/or counter electrode during a third time period.

6. A method according to claim 5 in which the charge passed is determined over a predetermined time period comprising at least one sub-period comprising a portion of the third time period.

7. A method according to claim 5, wherein charge passed is determined by measuring the current during the third time period or during one or more sub-periods comprising a portion of the third time period.

8. A method according to claim 5, wherein the reaction parameter is determined: (1) by calculating the difference between the total charge passed up to the start of the third time period and the total charge passed up to the end of the third time period and/or (2) by calculating the total charge passed during the third time period from charge passed during two or more sub-periods each comprising a portion of the third time period and as a whole comprising substantially all the third time period.

9. A method according to claim 5, wherein the reaction parameter is determined: (1) by calculating the magnitude of the difference between the total charge passed up to the start of the third time period and the total charge passed up to the end of the third time period and/or (2) by calculating the total charge passed during the third time period from charge passed during two or more sub-periods each comprising a portion of the third time period and as a whole comprising substantially all the third time period.

10. A method according to claim 1, wherein with respect to the counter electrode, the first oxidising potential is positive on the working electrode, and the reducing potential is negative on the working electrode.

11. A method according to claim 1, wherein the magnitude of the oxidising potential is greater than or equal to the magnitude of the reducing potential.

12. A method according to claim 1, wherein the duration of the first and second time periods are selected from at least one of the following groups:
   a first group in which the duration of the first time period is about 2 to about 9 seconds, about 3 to about 6 seconds, about 3 to about 5 seconds, 1 to 5 seconds, 2 to 9 seconds, 3 to 6 seconds, or 3 to 5 seconds;
   a second group in which the duration of the second time period is about 1 to about 9 seconds, about 2 to about 5 seconds, about 2 to about 4 seconds, 0.1 to 4 seconds, 1 to 9 seconds, 2 to 5 seconds, or 2 to 4 seconds;
   a third group in which the duration of the first time period is about 5 seconds and the duration of the second time period is about 4 seconds, the duration of the first time period is about 3 seconds and the duration of the second time period is about 2 seconds, the duration of the first time period is about 3 seconds and the duration of the second time period is about 1 second, or the duration of the first time period is 3 seconds and the duration of the second time period is 1 second;
   a fourth group in which the duration of the first time period is about 1 to about 3 seconds longer than the duration of the second time period, about 1 to about 2 seconds longer than the duration of the second time period, 1 to 3 seconds longer than the duration of the second time period, or 1 to 2 seconds longer than the duration of the second time period.

13. A method according to claim 1, wherein the reaction parameter is determined from one or more measurements made during a third time period which commences after the start of the second time period and wherein the duration of the third time period is selected from the group in which the duration of the third time period is: between about 0.05 seconds and about 2 seconds, between about 0.1 seconds and about 1 second, between about 0.2 seconds and 0.8 seconds, about 0.5 seconds or is between 0.05 and 2 seconds, between 0.1 and 1 second, between 0.2 and 0.8 seconds, 0.5 seconds, or the final 0.5 seconds of the second time period.

14. A method according to claim 1, wherein a ratio of an area of the counter electrode to an area of the working electrode is selected from the group in which the ratio is: at least 1.5 fold, at least 2 fold, at least 4 fold, at least 6 fold, at least 8 fold, or at least 10 fold.

15. A method according to claim 1, comprising:
providing a second working electrode and second counter electrode provided with mediator but not enzyme;
carrying out the method of claim 1 on the second working electrode and second counter electrode;
determining a background parameter indicative of the concentration of reduced mediator at the second counter electrode after commencement of the second time period; and
using the background parameter to correct one or more of the reaction parameter, the concentration of analyte, or a measurement parameter when said determining the reaction parameter comprises measuring a measurement parameter comprising one or more measurements.

16. A method according to claim 1, wherein a water soluble dry reagent film comprising enzyme and mediator is provided overlaying the working and counter electrodes, the dry reagent film having two exposed generally parallel opposing surfaces before being laid down.

17. A metering device configured to perform the method of claim 1, comprising:
a microprocessor configured to control application of an oxidizing potential between the working electrode and the counter electrode for a first time period, and a reducing potential between the working electrode and the counter electrode for a second time period, the first time period being of greater duration than the second time period; and
a detector configured to determine a reaction parameter indicative of the concentration of reduced mediator at the counter electrode after commencement of the second time period.

18. A kit comprising a metering device according to claim 17 and one or more of:
a sensor device having a substrate and having a working electrode and a counter electrode provided on the substrate in which the electrodes are both provided with an enzyme and mediator for carrying out a mediated redox reaction for use with the meter device;
instructions for carrying out the method of claim 1.

19. An apparatus for determining concentration of analyte in a fluid sample comprising:
a sensor device having a substrate and having a working electrode and a counter electrode provided on the substrate, in which both the working and counter electrodes are provided with an enzyme and a mediator;
and a metering device comprising
a microprocessor configured to control application of an oxidizing potential at a first voltage between the working electrode and the counter electrode for a first time period, and a reducing potential at a second voltage between the working electrode and the counter electrode for a second time period, the first time period being of greater duration than the second time period;
the metering device further comprising:
a detector to determine a reaction parameter indicative of the concentration of reduced mediator at the counter electrode after commencement of the second time period.

20. An apparatus according to claim 19 comprising the same or a different microprocessor for determining the concentration of analyte using the reaction parameter.

* * * * *